United States Patent
Torrence

(10) Patent No.: US 7,678,939 B2
(45) Date of Patent: Mar. 16, 2010

(54) ACETIC ACID PRODUCTION METHODS INCORPORATING TIN OR RUTHENIUM CATALYST STABILIZERS

(75) Inventor: G. Paull Torrence, League City, TX (US)

(73) Assignee: Celanese International Corporation, Dallas, TX (US)

( * ) Notice: Subject to any disclaimer, the term of this patent is extended or adjusted under 35 U.S.C. 154(b) by 0 days.

(21) Appl. No.: 11/807,254

(22) Filed: May 25, 2007

(65) Prior Publication Data

US 2007/0225521 A1    Sep. 27, 2007

Related U.S. Application Data

(63) Continuation-in-part of application No. PCT/US2006/004772, filed on Feb. 10, 2006.

(51) Int. Cl.
*C07C 53/08* (2006.01)
(52) U.S. Cl. .................................................. 562/607
(58) Field of Classification Search ....................... None
See application file for complete search history.

(56) References Cited

U.S. PATENT DOCUMENTS 5,939,585 A * 8/1999 Ditzel et al. ................ 562/519
6,211,405 B1 * 4/2001 Cheung et al. .............. 562/519
6,573,403 B1 * 6/2003 Joensen ...................... 562/519
2004/0122257 A1 * 6/2004 Cheung et al. .............. 562/519

FOREIGN PATENT DOCUMENTS

WO          0151444      *  7/2001

* cited by examiner

*Primary Examiner*—Karl J Puttlitz
(74) *Attorney, Agent, or Firm*—Martin Connaughton

(57) ABSTRACT

Processes for the production of acetic acid by carbonylation of methanol, and reactive derivatives thereof, in a reaction mixture using a rhodium-based catalyst system with at least one catalyst stabilizer selected from the group of ruthenium catalyst stabilizers, tin catalyst stabilizers, and mixtures thereof are provided. The catalyst stabilizers minimize precipitation of the rhodium metal during recovery of the acetic acid product, particularly in flasher units in an acetic acid recovery scheme. Stability of the rhodium metal is achieved even when the acetic acid is produced in low water content reaction mixtures in the presence of an iodide salt co-promoter at a concentration that generated an iodide ion concentration of greater than about 3 weight % of the reaction mixture. The stabilizing ruthenium or tin compounds may be present in the reaction mixture for the production of acetic acid at molar concentrations of ruthenium or tin metal to rhodium of about 0.1:1 to about 20:1.

17 Claims, 2 Drawing Sheets

| Hours | Control Run #1 Rh (ppm) | Ru Run #1 Rh (ppm) | Control Run #2 Rh (ppm) | Ru Run #2 Rh (ppm) |
|---|---|---|---|---|
| 0 | 1812 | 1917 | 1720 | 1917 |
| 24 | 806 | 1965 | 792 | 2039 |
| 48 | 553 | 1890 | 526 | 1988 |
| 72 | 455 | 1878 | 458 | 1935 |

ACETIC ACID PRODUCTION METHODS INCORPORATING TIN OR RUTHENIUM CATALYST STABILIZERS

PRIORITY

This application is a Continuation-in-Part of International Patent Application Serial No. PCT/US2006/004772 Filed Feb. 10, 2006 (publication no. WO 2006/091397) which application was based upon U.S. patent application Ser. No. 11/067,265 filed Feb. 24, 2005 entitled ACETIC ACID PRODUCTION METHODS INCORPORATING AT LEAST ONE METAL SALT AS A CATALYST STABILIZER, now U.S. Pat. No. 7,053,241. The priorities of the foregoing applications is hereby claimed, and their disclosures incorporated herein by reference.

FIELD OF THE DISCLOSURE

This invention relates to processes for the production of acetic acid using rhodium-based catalyst systems.

BACKGROUND INFORMATION

Large volumes of commercial acetic acid are produced by carbonylation of an alkyl alcohol, especially methanol, and reactive derivatives thereof, with carbon monoxide in a liquid reaction mixture. Such carbonylation reactions are generally carried out in the presence of a catalyst, often a Group VIII metal catalyst such as rhodium and iridium, a halogen-containing catalyst promoter, such as methyl iodide, and water. U.S. Pat. No. 3,769,329 to Paulik et al. discloses the use of a rhodium-based carbonylation catalyst dissolved, or otherwise dispersed, in a liquid reaction mixture or supported on an inert solid, along with a halogen-containing catalyst promoter as exemplified by methyl iodide. U.S. Pat. No. 3,769,329 to Paulik et al. discloses that water may be added to the reaction mixture to exert a beneficial effect upon the reaction rate, and water concentrations greater than 14 weight % of the reaction mixture are typically used. This is sometimes referred to as the "high water" carbonylation process.

An alternative to the "high water" carbonylation process is the "low water" carbonylation process, as described in U.S. Pat. Nos. 5,001,259 to Smith et al.; 5,026,908 to Smith et al.; and 5,144,068, also to Smith et al. Water concentrations in the reaction mixture of 14 weight % and lower may be used in the "low water" carbonylation process. Employing a low water concentration simplifies downstream processing of the desired carboxylic acid to its glacial form. The more water there is in a reaction stream, the greater the operating costs to remove water from the product acetic acid and the greater the capital investment in product recovery and purification equipment. The efficiencies achieved when operating at very low water concentrations makes it attractive to operate at the lowest water concentration possible.

However, while reducing the reactor mixture water concentration may minimize operating and fixed costs, it is more difficult to maintain catalyst stability and activity, as explained in U.S. Pat. Nos. 5,001,259 to Smith et al.; 5,026,908 to Smith et al.; and 5,144,068, also to Smith et al. In low water acetic acid production, especially in processes using rhodium-based catalysts, the catalyst metals tend to precipitate out of the reaction mixture. Catalyst precipitation is frequently experienced in product recovery systems, especially flasher units. Significant catalyst precipitation may lead to catalyst loss, reduced reaction rates, interrupted unit operation, and complete shutdowns. It is known that catalyst stability problems may be minimized by the use of a catalyst stabilizer such as a soluble metal iodide or quaternary iodide salt. As discussed in U.S. Pat. Nos. 5,001,259 to Smith et al.; 5,026,908 to Smith al.; and 5,144,068, also to Smith et al, especially suitable salts are alkali metal iodides such as lithium iodide since these are the most soluble and thermally stable in the reaction mixture. EP-A-0 161 874 to Smith et al. describes a reaction system in which methanol, is carbonylated to a carboxylic acid derivative such as acetic acid while using a liquid reaction mixture having low water content. The disclosure describes that this is achieved by the use of defined concentrations of an iodide salt, alkyl iodide and corresponding alkyl ester in the liquid reaction mixture to maintain rhodium catalyst stability and system productivity. EP 0 506 240 B1 to Watson discloses the introduction of one or more iodides of Group IA and IIA elements or hydrogen iodide into the flasher zone of an acetic acid recovery system. The introduction of the iodides is said to suppress the volatility of water relative to the acetic acid to aid in the recovery of the acetic acid.

Several patent references disclose the use of ruthenium, osmium, cadmium, mercury, zinc, gallium, indium, and tungsten for use as promoters in iridium catalyst systems. See, U.S. Pat. No. 5,510,524 to Garland et al.; EP 728 726 A1 to Garland et al.; EP 752 406 A1 to Baker et al.; EP 849 249 A1 to Ditzel et al.; and EP 849 250 A1 to Williams. Similarly, U.S. Pat. Nos. 6,458,996 to Muskett; 6,472,558 to Key et al.; and 6,686,500 to Watt and EP 643 034 A1 to Garland et al. mention the use of ruthenium and osmium as promoters for iridium catalyst systems. U.S. Published Patent Application 2004/0122257 to Cheung et al. discloses the use of salts of ruthenium, tungsten, osmium, nickel, cobalt, platinum, palladium, manganese, titanium, vanadium, copper, aluminum, tin, and antimony as catalyst co-promoters with rhodium catalyst systems in acetic acid production systems having less than 2 weight % water. U.S. Pat. No. 5,760,279 to Poole discloses the incorporation of a manganese stabilizer in conjunction with a rhodium catalyst. U.S. Pat. Nos. 4,433,166 to Singleton et al. and 4,433,165 to Singleton and EP 0 055618 to Singleton et al. disclose the use of tin as a rhodium catalyst system stabilizer used in high water carbonylation processes. The English language abstract of the publication entitled *Stabilization of Stannous Chloride for Rhodium Complexes Catalyst*, Journal of Xiamen University (Natural Science) Vol. 25 No 4 at pg. 488 (July 1986) also discloses the use of tin as a rhodium catalyst system stabilizer. The use of tin as a rhodium catalyst system stabilizer over certain temperature and pressure ranges is disclosed in the publication Zong, Xuezhang, et. al, *The Thermal Stability of Rh(I) Complex Catalyst In The Carbonylation of Methanol To Acetic Acid*, Southwest Res. Inst. Chem. Ind., Naxi, Peop. Rep. China. Cuihua Xuebao (1982), 3 (2), 110-16. CODEN: THHPD3 ISSN: 0253-9837. None of the references that disclose the use of ruthenium or tin as a rhodium catalyst system stabilizer or promoter disclose also the incorporation of the stabilizer in a low water system including an iodide ion, provided by an iodide salt, at concentrations of greater than 3 weight % of the reaction mixture.

EP 0 728 727 B1 to Poole et al. and equivalent U.S. Pat. No. 5,939,585 to Ditzel et al. disclose the use of ruthenium or osmium as a catalyst promoter to enhance production rates in combination with alkyl halide such as methyl iodide for the production or carboxylic anhydrides and acetic acid. The patent discloses that when carboxylic anhydrides are being produced, the iodide co-promoter may be selected as N,N' dimethyl imidazolium iodide or lithium iodide preferably present at concentrations up to its limit of solubility, for example 30 weight % lithium iodide. However, when acetic acid is produced, the references disclose that the iodide co-promoter may be lithium iodide but it should only be present at concentrations of less than 3 weight % lithium iodide. Such co-promoters will reduce the formation of volatile promoter species and thereby facilitate product recovery and purification. There is no mention of the use of lithium iodide as a stabilizer but only as a suppressant of volatility. However, the references note that the ruthenium or osmium promoters act as stabilizers for the rhodium catalyst at low partial pressures of carbon monoxide. Experiment "X" of EP 0 728 727 B1 to Poole et al. discloses 90.7% of rhodium precipitated in 23 hours without inclusion of ruthenium or osmium in an autoclave system. Example 33 of EP 0 728 727 B1 to Poole et al. discloses that inclusion of 20 molar equivalents of ruthenium trichloride hydrate per rhodium carbonyl chloride dimmer in the autoclave system reduced rhodium precipitation to 55.6% of rhodium from the solution.

Experiment H of EP 0 728 727 B1 to Poole et al. notes that the addition of lithium iodide to a reaction mixture for the production of acetic acid does not allow the reaction to remain constant. Therefore, as noted in Experiment H, ruthenium or osmium was not added to a reaction mixture containing lithium iodide. Presumably, because of the perceived rate destabilizing effects of lithium iodide in combination with low water conditions, EP 0 728 727 B1 to Poole et al. advises that when the ruthenium or osmium is added in combination with lithium iodide under low water conditions, it should only be done at lithium iodide concentrations of less than 3 weight %.

The publication *New Acetyls Technologies from BP Chemicals*, Science and Technology in Catalysis 1999, M. J. Howard, et al., pp. 61-68 reports "a non-commercial example" of, as described in EP 0 728 727 B1 to Poole et al. which is referenced in the publication, the use of ruthenium as a promoter to increase reaction rates in low water carbonylation systems using a rhodium catalyst. The use of another promoter, such as an iodide salt promoter, as a catalyst stabilizer, is not disclosed.

Published PCT Applications WO 2004/101487 to Gaemers et al. and WO 2004/101488 to Gaemers et al. disclose processes for production of acetic acid using rhodium and iridium metals coordinated with a polydentate ligand as catalyst systems. The published applications disclose the systems incorporating ruthenium, osmium, rhenium, cadmium, mercury, zinc, gallium, indium, and tungsten compounds as promoters. Molar ratios of the promoter to the rhodium or iridium of 0.1:1 to 20:1 are disclosed. Alkyl halide co-promoters are also disclosed. Additionally, water concentrations of 0.1 weight % to 10 weight % are disclosed. Finally, the published applications indicate that "an effective amount" of a stabilizer and/or promoter compound selected from alkali metal iodides, alkaline earth metal iodides, metal complexes capable of generating iodide ions, and salts capable of generating iodide ions may be incorporated. No specific information regarding the concentration of the "effective amount" is provided. The term "effective amount" is considered to refer to the iodide concentrations disclosed in the representative art as suitable for use in conjunction with ruthenium and tin compound promoters. In other words, iodide salt concentrations of less than 3 weight % are considered to represent an effective amount of the iodide compounds.

In summary, certain references disclose the use of various ruthenium and tin compounds as catalyst promoters and/or stabilizers. However, these references also disclose that the ruthenium and tin promoters and/or stabilizers are to be used only in systems incorporating low levels of iodide salt catalyst co-promoters or in the complete absence of iodide salt co-promoters.

SUMMARY OF THE DISCLOSURE

Figure 1:
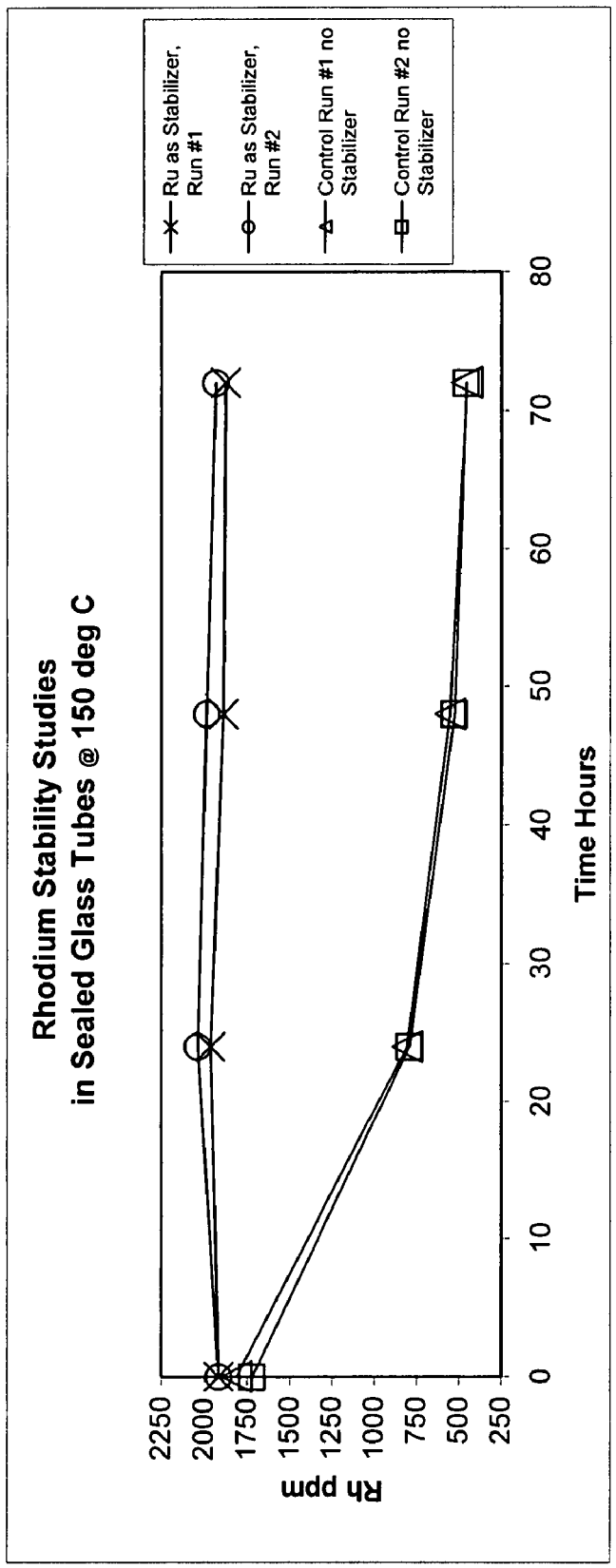
FIG. 1 represents the graphical form of the rhodium concentration of the ruthenium-containing solutions, and the control solutions existing at the outlined time intervals.

This disclosure relates to processes for the production of acetic acid by carbonylation of alkyl alcohols, reactive derivatives of alkyl alcohols, and mixtures of alkyl alcohols and reactive derivatives thereof in the presence of a rhodium-based catalyst system in conjunction with a halogen promoter, and an iodide salt co-promoter at an iodide concentration equivalent to greater than 3 weight %, in reaction mixtures having water concentrations of 0.1 weight % to 14 weight %. The processes incorporate at least one of a ruthenium catalyst stabilizer, a tin catalyst stabilizer, or mixtures thereof in the reaction mixture. The concentration levels of the iodide salt co-promoter described herein are higher than conventionally considered feasible for use in connection with stabilizers or promoters such as ruthenium and tin compounds.

At least one ruthenium catalyst stabilizer, tin catalyst stabilizer, or mixtures thereof stabilize the rhodium-based catalyst system and minimize precipitation of rhodium during recovery of the acetic acid product, particularly in flasher units in an acetic acid recovery scheme. Stability of the rhodium-based catalyst system is achieved even when acetic acid is produced in low water content reaction mixtures. The stabilizing ruthenium or tin compounds may be present in the reaction mixtures for the production of acetic acid at molar concentrations of metal to rhodium of about 0.1:1 to 20:1. The ruthenium or tin stabilizers may be combined with other catalyst stabilizers as well as catalyst promoters.

DETAILED DISCLOSURE

This disclosure relates generally to processes for producing acetic acid by carbonylation of alkyl alcohols, reactive derivatives of alkyl alcohols, and mixtures thereof. While the alkyl alcohol is ordinarily a feedstock, reactive derivatives such as halides, ethers or esters may be present in the feed or are formed in the reactor. A widely accepted proposed mechanism involves methyl iodide as the species which actually undergoes carbonylation when carbonylating methanol. Reactive derivatives of methanol include methyl acetate, dimethyl ether, methyl formate and methyl iodide. In particular, this disclosure relates to carbonylation processes taking place at water concentrations of about 0.1 weight % to about 14 weight % of the reaction mixture in which the carbonylation reaction takes place. Furthermore, the processes described herein relate to carbonylation reactions catalyzed by rhodium-based-catalyst systems in the presence of a halogen catalyst promoter, and an iodide salt catalyst co-promoter at an iodide concentration equivalent to greater than about 3 weight % in the reaction mixture. Finally, the processes described herein incorporate at least one ruthenium catalyst stabilizer, at least one tin catalyst stabilizer, or mixtures thereof in the reaction mixture to stabilize the rhodium-based catalyst systems incorporating the halogen promoter and the iodide salt catalyst co-promoter.

An important aspect of the processes described herein is the improved catalyst stability provided by the unique combination of the halogen catalyst promoter, the iodide salt co-promoter, and the ruthenium and/or tin stabilizer used in a low water carbonylation environment. In this unique combination the iodide salt co-promoter is present at a concentrations of greater than about 3 weight % in the reaction mixture. In particular, the concentration of the iodide salt co-promoter described herein is higher than iodide salt co-promoters concentrations previously thought to be suitable for use in conjunction with ruthenium and/or tin stabilizers or promoters. It is the combination of these three components in a low water environment with the iodide salt co-promoter present at the described concentrations that provides unexpected enhanced catalyst stability.

In certain embodiments, the water concentrations in the reaction mixtures in the processes described herein are from about 1 weight % to 14 weight %. In certain other embodiments, the water concentrations in the reaction mixtures in the processes described herein are from about 1 weight % to about 8 weight %. In other embodiments, the water concentrations in the reaction mixtures in the processes described herein are from about 1 weight % to about 6 weight %. In still other embodiments, the water concentrations in the reaction mixtures in the processes described herein are from about 1 weight % to about 4 weight %.

The incorporation of at least one of the ruthenium or tin stabilizers in the reaction mixture reduces the tendency of rhodium in the rhodium-based catalyst system to precipitate out of solution during the production and purification of acetic acid. Rhodium compounds are particularly susceptible to instability leading to precipitation of the rhodium catalyst as $RhI_3$ during recovery of acetic acid, particularly in the flasher unit. Rhodium is a very expensive metal and loss of the metal through precipitation may have significant negative financial impact on commercial acetic acid production processes by affecting catalyst usage and maintenance of high production.

Although, as discussed above, the use of ruthenium and tin as catalyst promoters or stabilizers in certain systems is known, none of the known systems discloses the use of ruthenium or tin as rhodium catalyst stabilizers in combination with a halogen promoter and high iodide salt co-promoter concentrations, as defined herein, under low water conditions. The processes described herein recognize that this unique combination of carbonylation system components provides significant stability to rhodium-based catalyst systems. As discussed, the processes described herein relate to the use of rhodium-based catalyst systems. For purposes of this disclosure, a "rhodium-based catalyst system" or "rhodium-based catalyst" means a catalyst system providing a rhodium metal concentration in a methanol carbonylation reaction mixture of at least 300 ppm.

In certain embodiments, the rhodium-based catalyst systems described herein provide from about 300 ppm to about 5,000 ppm of rhodium in the reaction mixture. In other embodiments, the rhodium-based catalyst systems described herein provide from about 1,000 ppm to about 4,000 ppm of rhodium in the reaction mixture. In still other embodiments, the rhodium-based catalyst systems described provide from about 2,000 ppm to about 3,000 ppm of rhodium in the reaction mixture. In certain embodiments, the rhodium concentration in the reaction mixture is at least 1000 ppm. In other embodiments, the rhodium concentration in the reaction mixture is at least 1500 ppm. In still other embodiments, the rhodium concentration in the reaction mixture is at least 2000 ppm.

In addition to rhodium, the reaction mixtures of the processes described herein also include a halogen promoter, such as a hydrogen iodide or organic iodide and an iodide salt co-promoter. In certain embodiments, the organic iodide is an alkyl iodide such as methyl iodide. The halogen promoter may be present in the reaction mixture at a concentration of about 2.0 weight % to about 30 weight %. In other embodiments, the halogen promoter is present at a concentration in the reaction mixture of about 5.0 weight % to about 15 weight %. In still another embodiment, the halogen promoter is present in the reaction mixture at a concentration of about 5 weight % to about 10 weight %.

The iodide salt co-promoter used in the reaction mixtures of the processes described herein may be in the form of a soluble salt of an alkali metal or alkaline earth metal or a quaternary ammonium or phosphonium salt. In certain embodiments, the catalyst co-promoter is lithium iodide, lithium acetate, or mixtures thereof. The salt co-promoter may be added as a non-iodide salt that will generate an iodide salt. The iodide catalyst stabilizer may be introduced directly into the reaction system. Alternatively, the iodide salt may be generated in-situ since under the operating conditions of the reaction system, a wide range of non-iodide salt precursors will react with methyl iodide to generate the corresponding co-promoter iodide salt stabilizer. For additional detail regarding iodide salt generation, see U.S. Pat. Nos. 5,001,259 to Smith et al.; 5,026,908 to Smith et al.; and 5,144,068, also to Smith et al.

The concentration of the co-promoter is such that it generates an iodide ion concentration in the reaction mixture of greater than about 3 weight %. In still other embodiments, the concentration of the co-promoter is such that it generates an iodide ion concentration in the reaction mixture of about 4 weight % to about 20 weight %. In additional embodiments, the concentration of the co-promoter is such that it generates an iodide ion concentration in the reaction mixture of about 5.0 weight % to about 20 weight %. In other embodiments, the concentration of the co-promoter is such that it generates an iodide ion concentration in the reaction mixture of about 10 weight % to about 20 weight %. In still other embodiments, the concentration of the co-promoter is such that it generates an iodide ion concentration in the reaction mixture of about 5 weight % to about 10 weight %.

As discussed above, the reaction mixtures of the processes disclosed herein also incorporate at least one ruthenium catalyst stabilizer, at least one tin catalyst stabilizer, or mixtures thereof in the reaction mixture to stabilize the rhodium-based catalyst systems. The stabilizing metal compounds may be present in the reaction mixtures at molar concentrations of metal to rhodium of about 0.1:1 to about 20:1. In other embodiments, the stabilizing metal compounds may be present in the reaction mixtures at molar concentrations of total ruthenium and tin to rhodium of about 0.5:1 to about 10:1. In still other embodiments, the stabilizing metal compounds may be present in the reaction mixtures at molar concentrations of total metals to rhodium of 1:1 to 5:1.

Ruthenium and tin salts suitable for use as catalyst stabilizers as described herein include halide, acetate, nitrate, oxide, and ammonium salts of ruthenium and tin, while other forms may be used as noted below.

Suitable tin compounds which may be added to the reaction mixture include: tin metal, stannous chloride, stannous oxide, organo tin compounds, such as tetraalkyl tin, stannic chloride, stannic oxide, stannous acetate and the like. The valence of the tin catalyst stabilizer compound added may be any suitable value.

Specific examples of ruthenium compounds suitable for the practice of this invention include halide-containing ruthenium salts such as ruthenium(III) trihalides, and ruthenium carbonyl halides. Iodides are preferred halides. Alternatively, the ruthenium catalyst stabilizer may be prepared by adding the ruthenium to the reaction mixture in an oxide form, as in the case of, for example, ruthenium(IV) dioxide hydrate, anhydrous ruthenium(IV) dioxide and ruthenium(VIII) tetraoxide. It may be introduced into the reaction zone also as the salt of a mineral acid, as in the case of ruthenium(III) chloride hydrate, ruthenium(III) bromide, anhydrous ruthenium(III) chloride and ruthenium nitrate, or as the salt of a suitable organic carboxylic acid. Here, examples include ruthenium acetate dimer, ruthenium propionate dimer, ruthenium hexafluoroacetylacetonate, ruthenium trifluoroacetate dimer, ruthenium octanoate dimer, ruthenium naphthenate, ruthenium valerate and ruthenium(III) acetylacetonate. The ruthenium may also be further added to the reaction zone as a carbonyl or hydrocarbonyl derivative. Suitable examples in this case include triruthenium dodecarbonyl, hydrocarbonyls such as $H_2Ru_4(CO)_{13}$ and $H_4Ru_4(CO)_{12}$ and substituted carbonyl species such as ruthenium tricarbonyl trichloride.

Without intending to be bound by any theory, it is believed ruthenium and tin compounds are converted in-situ in the reactor (at least in part) to an iodide and/or acetate containing compound. Therefore, the identity of the ruthenium or tin compounds added to the reaction mixture to stabilize the rhodium metal may vary. For purposes of this disclosure, references to the concentration or molar ratios of the ruthenium and tin compounds refers to the total of all forms of the ruthenium and tin, regardless of form. For molar ratios, the molar ratio of the ruthenium or tin is, of course, governed by the concentration of the respective metal, regardless of the form in which it exists.

To provide carbonylation reactions as described herein, all selected reaction mixture components are dissolved or dispersed in the reaction mixture vessel or reactor. During a period of active reaction, methanol and carbon monoxide are continuously fed to the reactor containing a reaction mixture in which a desired partial pressure of carbon monoxide is maintained. The carbonylation reactor is typically a stirred autoclave within which the reacting liquid components are maintained at a constant level. Into the reactor, there are continuously introduced fresh methanol, sufficient water to maintain the desired concentration of water in the reaction medium, recycled catalyst solution from the flasher base, and typically recycled methyl iodide and methyl acetate from an overhead of the methyl iodide-acetic acid splitter column. In certain embodiments, the methyl acetate is maintained in the reaction mixture at a concentration of about 0.5 weight % to about 30 weight %. Alternate distillation systems can be employed so long as a means is provided for recovering the crude acetic acid and recycling to the reactor catalyst solution, methyl iodide, and methyl acetate. Carbon monoxide is continuously introduced into the reactor just below the agitator which is used to stir the contents. The carbon monoxide is thoroughly dispersed through the reaction mixture. A gaseous purge stream is vented from the head of the reactor to prevent buildup of gaseous by-products and to maintain a set carbon monoxide partial pressure at a given total reactor pressure. The temperature of the reactor is controlled, and the carbon monoxide is introduced at a rate sufficient to maintain a constant total reactor pressure. The total reactor pressure is from about 1.5 MPa to about 4.5 MPa absolute, with the reaction temperature typically maintained from about 150° C. to about 250° C.

Liquid product is drawn off the carbonylation reactor at a rate sufficient to maintain a constant level of the reaction mixture and is introduced to a flasher unit. In the flasher unit, a catalyst solution is withdrawn as a base stream incorporating predominantly acetic acid containing rhodium catalyst, the iodide salt co-promoter, and the ruthenium and/or tin stabilizer, along with lesser quantities of methyl acetate, the halogen promoter, and water. An overhead stream from the flasher comprises predominately product acetic acid along with methyl iodide, methyl acetate, and water. A portion of the carbon monoxide along with gaseous by-products such as methane, hydrogen, and carbon dioxide exit the top of the flasher. For additional information regarding acetic acid production systems and schemes, see U.S. Pat. Nos. 4,433,166 to Singleton et al.; 5,144,068 to Smith et al.; and 6,677,480 to Huckman et al. For more information regarding specific process for producing acetic through carbonylation reactions, see the publication: Graub, M., Seidel, A., Torrence, P., Heymanns, P., Synthesis of Acetic Acid and Acetic Acid Anhydride from Methanol. Applied Homogeneous Catalysis with Organometallic Compounds. (1996), Volume 1, 104-138. Editor(s): Cornils, B., Herrmann, W., Publisher: VCH, Weinheim, Germany.

As discussed above, rhodium catalyst precipitation is frequently experienced in product recovery systems, especially flasher units. The benefits of the systems described herein in reducing rhodium catalyst precipitation are exemplified by the following experimental evaluations.

Experimental Evaluations

Rhodium catalyst stability experiments were conducted under a nitrogen ($N_2$) atmosphere in sealed pressure glass tubes. The sealed pressure glass tubes were equipped with controlled temperature and stirring using a pressure tube reactor system made by Genevac (RS 1000 Reaction Station). Stock rhodium catalyst solutions incorporating 1,500 ppm to 2,000 ppm Rh, containing 15 weight % lithium iodide (LiI) in an approximately 2 weight % to 4 weight % aqueous acetic acid medium were prepared in a Fisher-Porter glass apparatus. The stock solutions were purged with carbon monoxide (CO) at 125° to 150° C. and a pressure of 241.1 kPa with stirring for one hour to ensure complete dissolution of the rhodium catalyst complex before conducting catalyst precipitation tests. The prepared catalyst solutions were cooled and then purged with $N_2$ for one hour to remove dissolved CO before placing the catalyst solutions into glass tubes which were sealed under a $N_2$ atmosphere. These solutions simulate the CO partial pressure in the flasher unit. The rhodium concentration for the stock solution and the test solutions were determined by atomic absorption (AA) spectroscopy.

Three types of the catalyst solutions were prepared as outlined above. The first type of solution was a control solution without a ruthenium or tin stabilizer and 15 weight % lithium iodide. A second type solution contained 15 weight % lithium iodide and a ruthenium salt added as $RuI_3$ at a molar ratio of ruthenium to rhodium of 5:1. A third type of solution included 15 weight % lithium iodide and a tin salt added as $SnI_2$ at molar ratios of tin to rhodium of 10:1.

The prepared solution were maintained for 72 hours in the sealed glass tubes at conditions simulating flasher conditions, at temperature of 150° C. and 241.1 kPa under a $N_2$ atmosphere. Rhodium concentrations in each solution were determined at 24 hours, 48 hours, and 72 hours intervals.

Two solutions containing a ruthenium stabilizer were tested simultaneously with a control solution that contained no ruthenium or tin stabilizer. The rhodium concentration of the ruthenium containing solutions and the control solutions existing at the outlined time intervals over time are reported in numerical and graphical forms in FIG. 1.

Two solutions containing the tin stabilizer were tested simultaneously with a control solution that contained no ruthenium or tin. The rhodium concentration of each tin containing solution and the control solutions existing at the outlined time intervals over time are reported in numerical and graphical forms in FIG. 2.

Figure 2:
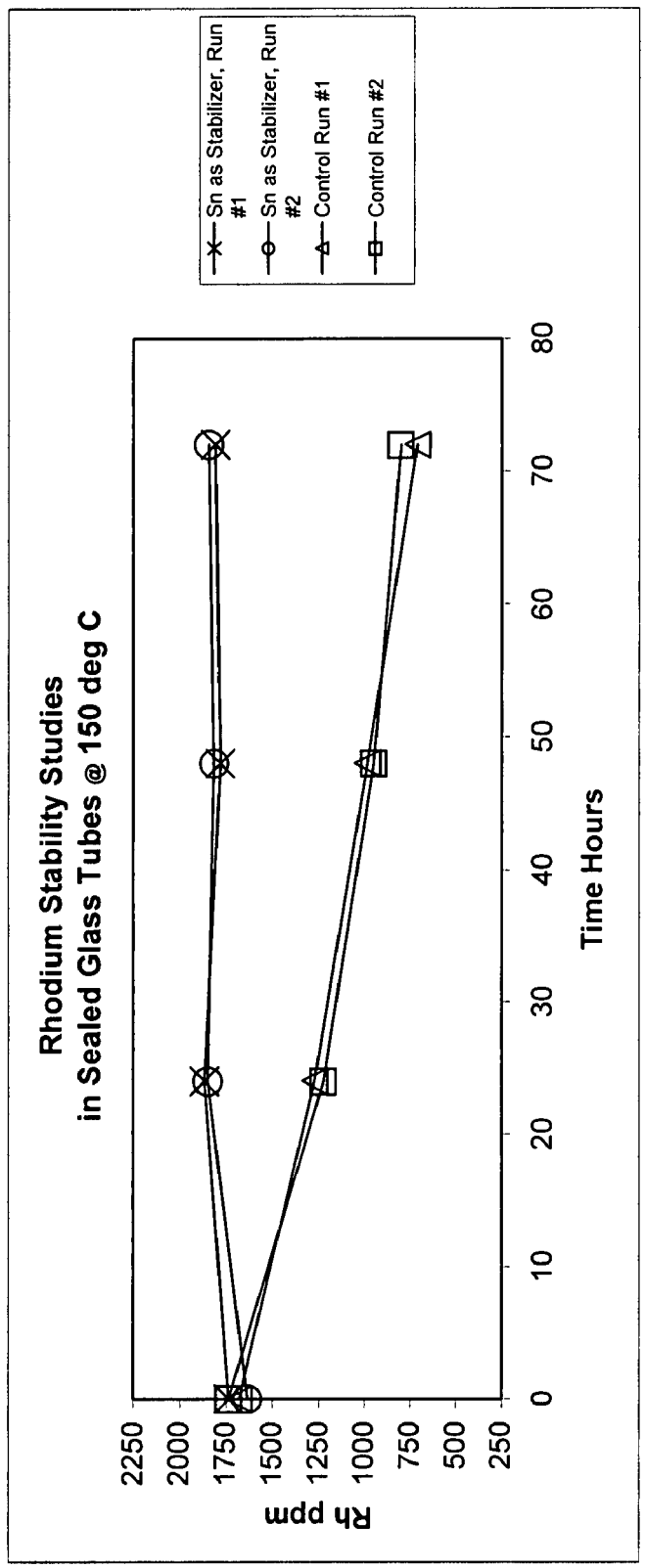
FIG. 2 represents the graphical form of the rhodium concentration of the tin-containing solutions and the control solutions existing at the outlined time intervals.

With reference to FIG. 1 and FIG. 2, it was observed that the presence of the ruthenium and tin salts in the rhodium catalyst solutions significantly reduced the rate of $RhI_3$ precipitation over time. In particular, it is seen that in the solutions in which no ruthenium or tin salt was present, approximately 50% to 70% of the soluble Rh precipitated as $RuI_3$ by the end of each 72 hour period. It is observed that in the solutions incorporating ruthenium and tin salts, no significant $RuI_3$ precipitation occurred over the 72 hour periods.

Comparing the results reported in FIG. 1 and FIG. 2, discussed above, to the stabilization results reported in EP 0 728 727 B1 to Poole et al. in experiment X and example 33, it is seen that the systems described herein incorporating an iodide ion at concentrations greater than about 3 weight % in combination with ruthenium or tin exhibited dramatically better stabilization than the systems incorporating ruthenium without an iodide ion as reported in EP 0 728 727 B1 to Poole et al.

With respect to the various ranges set forth herein, any upper limit recited may, of course, be combined with any lower limit for selected sub-ranges.

All patents and publications, including priority documents and testing procedures, referred to herein are hereby incorporated by reference in their entireties.

Although the processes described herein, and the advantages thereof, have been described in detail, it should be understood that various changes, substitutions, and alterations could be made without departing from the spirit and scope of the processes described herein, as defined by the following claims.

What is claimed is:

1. A process for the production of acetic acid, by a catalytic carbonylation reaction, comprising reacting a compound selected from the group consisting of an alkyl alcohol and reactive derivatives thereof in a reaction mixture, in the presence of carbon monoxide and a rhodium-based catalyst system comprising: (i) rhodium; (ii) a halogen promoter; (iii) an iodide salt co-promoter at a concentration that generates an iodide ion concentration of greater than about 3 weight % of the reaction mixture; and (iv) a ruthenium or tin catalyst stabilizer or mixture thereof; wherein the reaction mixture comprises from about 0.1 weight % to about 14 weight % water, and wherein the ruthenium catalyst stabilizer, the tin catalyst stabilizer, or mixtures thereof are present in a molar ratio of combined ruthenium and tin to rhodium in the reaction mixture of from 5:1 to about 20:1.

2. The process of claim 1 wherein rhodium is present in the reaction mixture at a concentration of 300 ppm to 5,000 ppm of the reaction mixture.

3. The process of claim 1 wherein a halogen promoter is present in the reaction mixture at a concentration of about 2 weight % to about 30 weight % in the reaction mixture.

4. The process of claim 1 wherein the reaction mixture comprises from 2 weight % to 8 weight % water.

5. The process of claim 1 wherein the catalyst stabilizer consists essentially of the ruthenium catalyst stabilizer.

6. The process of claim 1 wherein the alkyl alcohol is methanol and the reaction mixture comprises from about 2 weight % to about 6 weight % water.

7. The process in accordance with claim 1 wherein the halogen promoter is methyl iodide and is present at a concentration of about 5 weight % to about 15 weight % of the reaction mixture.

8. The process in accordance with claim 1 wherein the reaction mixture comprises from about 0.5 weight % to about 30 weight % methyl acetate and the iodide salt co-promoter is lithium iodide and is present at a concentration that generates an iodide ion concentration of about 4 weight % to about 20 weight % of the reaction mixture.

9. The process of claim 1 wherein the reaction mixture comprises at least 1000 ppm of rhodium and the molar ratio of ruthenium and/or tin to rhodium in the reaction mixture is from 5:1 to about 10:1.

10. The process of claim 1 wherein water is present in the reaction mixture at a concentration of about 1 weight % to about 4 weight % of the reaction mixture.

11. The process of claim 1 wherein the ruthenium catalyst stabilizer and the tin catalyst stabilizer are respective salts selected from the group consisting of iodide salts, acetate salts, and mixtures thereof.

12. The process of claim 1 wherein the reaction mixture comprises at least 1500 ppm of rhodium.

13. The process of claim 12 wherein methyl iodide is present from about 5 weight % to about 10 weight % of the reaction mixture and lithium iodide is present at a concentration that generates an iodide ion concentration of about 5 weight % to about 10 weight % of the reaction mixture.

14. The process of claim 13 wherein the reaction mixture comprises at least 2000 ppm of rhodium.

15. The process of claim 12 wherein the catalyst stabilizer includes a ruthenium salt present in a molar ratio of ruthenium to rhodium in the reaction mixture of from 5:1 to about 10:1.

16. The process of claim 12 wherein the catalyst stabilizer consists essentially of a ruthenium salt present in a molar ratio of ruthenium to rhodium in the reaction mixture of from 5:1 to about 10:1.

17. The process of claim 12 wherein the catalyst stabilizer includes a tin salt present in a molar ratio of tin to rhodium in the reaction mixture of from 10:1 to about 20:1.

* * * * *